(12) United States Patent
Henriksen et al.

(10) Patent No.: US 6,391,342 B1
(45) Date of Patent: May 21, 2002

(54) PHARMACEUTICAL FORMULATION COMPRISING A 2- [(2-PYRIDINYL) METHYL] SULFINYL BENZIMIDAZOLE HAVING ANTI-ULCER ACTIVITY AND A PROCESS FOR THE PREPARATION OF SUCH FORMULATION

(75) Inventors: Kristian Lund Henriksen, Søborg; Helle Kann, Frederiksberg; Karen Eichstedt Sørensen, Valby; Søren Bols Pedersen, Hvidovre, all of (DK)

(73) Assignee: A/S GEA Farmaceutisk Fabrik, Frederiksberg (DK)

( * ) Notice: Subject to any disclaimer, the term of this patent is extended or adjusted under 35 U.S.C. 154(b) by 0 days.

(21) Appl. No.: 09/646,486

(22) PCT Filed: Mar. 17, 1999

(86) PCT No.: PCT/DK99/00137

§ 371 Date: Sep. 19, 2000

§ 102(e) Date: Sep. 19, 2000

(87) PCT Pub. No.: WO99/48498

PCT Pub. Date: Sep. 30, 1999

(30) Foreign Application Priority Data

Mar. 20, 1998 (DK) ................................ 0397/98

(51) Int. Cl.[7] .............................. A61K 9/50; A61K 9/16; A61K 9/52; A61K 9/64; A61K 9/54
(52) U.S. Cl. ..................... 424/490; 424/457; 424/458; 424/456; 424/489; 424/498
(58) Field of Search ................................ 424/490, 457, 424/458, 456, 502, 489

(56) References Cited

FOREIGN PATENT DOCUMENTS

| | | | |
|---|---|---|---|
| EP | 0 124 495 | 2/1984 | |
| EP | 0 237 200 | 2/1987 | .......... A61K/31/44 |
| EP | 0 423 748 | 2/1987 | .......... A61K/31/44 |
| EP | 0 446 961 | 2/1987 | .......... A61K/31/44 |
| EP | 0 244 380 | 4/1987 | ........... A61K/9/32 |
| EP | 0 247 983 | 4/1987 | .......... A61K/31/44 |
| EP | 0496 437 | 4/1987 | .......... A61K/31/44 |
| EP | 0 277 741 | 1/1988 | ............ A61K/9/16 |
| EP | 0 519 144 | 6/1991 | ............ A61K/9/54 |
| EP | 0 514 008 | 4/1992 | ............ A61K/9/16 |
| EP | 0 589 981 | 6/1992 | ............ A61K/9/20 |
| EP | 94/02140 | 7/1992 | .......... A61K/31/44 |
| EP | 0 630 235 | 3/1993 | ............ A61K/9/16 |
| EP | 96/24338 | 2/1995 | ............ A61K/9/30 |
| ES | 2 024 993 | 3/1992 | ............ A61K/9/56 |
| ES | 2 087 823 | 7/1994 | .......... A61K/31/44 |
| PT | 101 826 | 2/1996 | |
| WO | 93/25204 | 6/1992 | .......... A61K/31/44 |
| WO | 97/12581 | 9/1992 | |
| WO | 96/31213 | 4/1995 | .......... A61K/31/44 |
| WO | 96/37195 | 5/1995 | ............ A61K/9/16 |
| WO | 96/23500 | 1/1996 | .......... A61K/31/44 |
| WO | 97/25065 | 1/1996 | .......... A61K/45/06 |
| WO | 97/12580 | 9/1996 | |
| WO | WO-97/12581 A2 * | 4/1997 | |
| WO | 98/40377 | 9/1998 | ......... C07D/401/12 |

* cited by examiner

Primary Examiner—Thurman K. Page
Assistant Examiner—Rachel M. Bennett
(74) Attorney, Agent, or Firm—Cohen, Pontani, Lieberman & Pavane

(57) ABSTRACT

Oral pharmaceutical formulation comprising granules having an inert core coated with a layer, comprising a 2-[[(2-pyridinyl)methyl]sulfinyl]benzimidazole having anti-ulcer activity, a disintegrant and a surfactant in a matrix of a melt coating substance essentially consisting of one or more esters of glycerol and fatty acids, a separating layer and an enteric coating layer, and a process for the preparation of such formulation using a melt coating technique for the preparation of the benzimidazole containing layer.

37 Claims, No Drawings

PHARMACEUTICAL FORMULATION COMPRISING A 2-[(2-PYRIDINYL) METHYL] SULFINYL BENZIMIDAZOLE HAVING ANTI-ULCER ACTIVITY AND A PROCESS FOR THE PREPARATION OF SUCH FORMULATION

This application is a 371 of PCT/DK99/00137 filed Mar. 17, 1999.

The present invention relates to an oral pharmaceutical formulation comprising a 2-[[(2-pyridinyl)methyl]sulfinyl] benzimidazole having anti-ulcer activity as active ingredient, and a process for the preparation of such formulation.

2-[[(2-pyridinyl)methyl]sulfinyl]benzimidazoles having anti-ulcer activity is a well-known group of compounds which have been extensively described in the literature, and a substantive number of patents and patent applications have been directed to such compounds, to processes for their preparation and to formulations containing them as active ingredient.

The compounds prepared according to our international patent application No. PCT/DK98/00058 are examples of such compounds, viz the 2-[[(2-pyridinyl)methyl]sulfinyl]-1H-benzimidazole derivatives of the general formula I

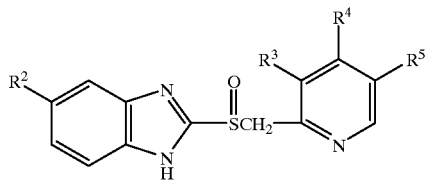

wherein
R² represents H, OCH₃, OCHF₂ or CF₃,
R³ represents H, CH₃ or OCH₃,
R⁴ represents H, OCH₃, OCH₂CF₃ or halo, such as Cl, Er or F, and
R⁵ represents H, CH₃ or OCH₃, and salts thereof.

Specific examples are the compounds, 5-methoxy-2-[[(4-methoxy-3,5-dimethyl-2-pyridinyl)methyl]sulfinyl]-1H-benzimidazole (omeprazole), 2-[[[4-(2,2,2-trifluoroethoxy)-3-methyl-2-pyridinyl]methyl]sulfinyl]-1H-benzimidazole (lansoprazole), 2-[[(2-pyridinyl)methyl]-sulfinyl]-1H-benzimidazole (timoprazole) and 5-di-fluoromethoxy-2-[[(3,4-dimethoxy-2-pyridinyl)methyl]-sulfinyl]-1H-benzimidazole (pantoprazole), among which omeprazole, lansoprozole and pantoprazole are presently being marketed in Denmark as gastric acid secretion inhibiting agents, e.g. for the treatment and prophylaxis of gastric and duodenal ulcers, reflux oesophagitis and Zollinger-Ellison's syndrome.

In the following the invention will be explained with particular reference to omeprazole, however it should be understood, that the invention is not limited to an omeprazole containing formulation.

As is known in the art, omeprazole is sensible to acids, but very soluble in alkaline solutions and only slightly soluble in water. Furthermore, omeprazole is known to be sensible to humidity, heat, light and organic solvents.

Consequently oral formulations of omeprazole and other 2-[[(2-pyridinyl)methyl]sulfinyl]benzimidazoles have been provided with an enteric coating for protection of the active ingredient against degradation by the gastric acid in the stomach and release of the active ingredient in the proximal part of the small intestine.

An oral formulation of omeprazole based on pellets provided with an enteric coating, and results of bioavailability tests carried out with such pellet formulation is described in Scand. J. Gastroenterol., 1985, 20 (suppl. 108), pp. 113–120, Pilbrandt Å. and Cederberg C., "Development of an oral formulation of omeprazole". However, the stability of this type of formulation is not satisfactory, and degradation of the omeprazole is observed, among others due to the acidic nature of the enteric coating.

In an attempt to improve the stability of omeprazole, certain alkaline salts of omeprazole have been prepared, cf. EP 0 124 495 A. Similarly, EP 0 237 200 B1, EP 0 423 748 B1 and EP 0 446 961 B1, the two later being based on divisional applications of the former, use basic inorganic salts of magnesium and/or calcium to improve the stability of 2-[[(2-pyridinyl)methyl]sulfinyl]benzimidazoles having anti-ulcer activity.

However, it has also been described that when such alkaline cores are provided with an enteric coating of a conventional enteric coating polymer such as, e.g., cellulose acetate phthalate, water from the gastric juice may diffuse through the coating while the dosage form resides in the stomach and dissolve the core partially in the close proximity of the enteric coating. Here it will form an alkaline solution which will attack the enteric coating from the inside and eventually dissolve it.

In order to solve this problem EP 0 247 983 B1 and EP 0 496 437 B1, the later being based on a divisional application of the former, suggest providing enteric coated small alkaline reacting cores, which as the active component contains omeprazole together with an alkaline reacting compound, or an alkaline salt of omeprazole optionally together with an alkaline reacting compound, with a subcoating comprised of one or more inert reacting subcoating layers comprising tablet excipients which are soluble or rapidly disintegrating in water, or polymeric, water-soluble, film-forming compounds, optionally containing pH-buffering alkaline compounds. The subcoating separates the alkaline reacting cores from the enteric coating. Hydroxypropyl methylcellulose, hydroxypropyl cellulose and polyvinylpyrrolidone are mentioned as examples of materials for the subcoating.

Corresponding formulations based on other acid labile benzimidazoles are disclosed in EP 0 244 380 B1.

According to WO 96/24338 a water soluble separating layer comprising a water soluble salt of an enteric coating polymer is formed in situ between an alkaline reacting core material containing a proton pump inhibitor, such as omeprazole, lansoprazole or pantoprazole, and an enteric coating. The alkaline reacting core may be prepared in different ways, such as by preparation of granules or tablets including the active substance and the alkaline reacting compound(s) or by application of a layer including the active substance and the alkaline reacting compounds) to preformed seeds.

WO 94/02140 describes an enteric pharmaceutical composition comprising a core containing an anti-ulcer agent, such as omeprazole or lansoprazole, an undercoating of one or two layers and an enteric coating, wherein the core and/or the undercoating comprises aluminium hydroxide.sodium bicarbonate coprecipitate optionally in mixture with a buffer, or a mixture of one of the following with a buffer: aluminium glycinate, an amino acid, an acid salt of an amino acid and an alkali salt of an amino acid, as a stabilizer, the buffers used being capable of controlling the pH of the mixtures to 8–9.

ES 2 024 993 describes an oral pharmaceutical composition comprising a core including omeprazole or an alkaline salt thereof in combination with a basic compound, a first coating made from an inert water soluble excipient and a second basic compound, and a second coating being an enteric coating. As examples of basic compounds which may be included in the composition, sodium, potassium, magnesium, calcium, aluminium and dihydroxy aluminium salts of amino acids or a pyridine carboxylic acid are mentioned. Furthermore the known anti-ulcer agents ranitidine and famotidine are mentioned as examples of the basic compounds which may be added to the core.

EP 0 277 741 A1 describes a method for producing spherical granules having a core being coated with spraying powder containing a drug and low substituted hydroxypropyl cellulose while being sprayed with an aqueous binder, such as a 1% (w/v) solution of hydroxypropyl cellulose. By the process spherical granules being excellent in hardness and disintegration are said to be obtained. The coated cores may be coated with further coatings; sustained release coatings, gastric coatings and enteric coatings being mentioned as examples. Benzimidazoles having anti-ulcer activity are mentioned as examples of the drug and in Examples 1 and 10 lansoprazole is used as the drug. However, it is noted that in both examples, lansoprazole is utilized in combination with a very substantive amount of the alkaline stabilizer, magnesium carbonate.

WO 96/23500 describes an oral pharmaceutical formulation containing a benzimidazole compound, which is labile in acid medium, e.g. omeprazole and lansoprazole, which is obtained by coating inert cores with a first layer containing the benzimidazole compound, a water-soluble inert polymer such as hydroxypropyl methylcellulose or hydroxypropyl cellulose, and pharmaceutically acceptable excipients having a non-alkaline reaction, such as talc, followed by coating with a second layer comprising an inert water-soluble polymer such as hydroxypropyl methylcellulose or hydroxypropyl cellulose, talc and a pigment such as titanium dioxide, and finally with a third enteric layer comprising a polymer which is resistant to gastric juice, such as copolymerized methacrylic acid/methyl methacrylate, a plasticizer such as triethyl citrate or the like, and talc. The layers are applied using aqueous solutions or dispersions.

Similarly WO 97/12580 and WO 97/12581 broadly describe compositions exempt of alkaline-reacting compounds, which comprise a core containing an acid-labile benzimidazole active principle, said core being constituted of nuclei and the active ingredient mixed together and then compressed together, the active principle not being in the form of an alkaline salt; an intermediate layer; and an enteric layer. In the claims of WO 97/12581 the benzimidazole is restricted to omeprazole, whereas omeprazole is disclaimed in WO 97/12580.

The specific nuclei used in the examples are lactose nuclei and the cores are prepared by application of a suspension of the benzimidazole in an aqueous solution of hydroxypropyl methylcellulose to the nuclei by spraying followed by drying. A surfactant like Polysorbate 80 or sodium lauryl sulfate may be added to the suspension. The dried nuclei are mixed with crospovidone and a lubricant and the obtained mixture is compressed into microtablets, which are coated with an intermediate layer and an enteric layer.

EP 0 589 981 B1 describes an oral gastric juice resistant pantoprazole formulation in the form of pellets or tablets comprising a core containing pantoprazole or a salt thereof, polyvinylpyrrolidone and/or hydroxypropyl methylcellulose as a binder, optionally mannitol as a filler, optionally other adjuvants and one or more basic inorganic compounds; one or more water-soluble intermediate coatings; and a gastric juice resistant outer coating.

The basic inorganic compounds are added for providing a basic reaction to the core if not already provided through the use of a salt of the pantoprazole. Water or a mixture of water and isopropanol is used as medium during the preparation of the pantoprazole containing core.

EP 0 519 144 A1 describes a process for the preparation of an omeprazole containing preparation, whereby inert cores are coated with three layers. The first layer is obtained using an aqueous dispersion of omeprazole, hydroxypropyl methylcellulose, lactose, L-hydroxypropyl cellulose, sodium lauryl sulfate and the alkaline substance, disodium hydrogen phosphate dihydrate. For the second layer an aqueous dispersion of hydroxypropyl methylcellulose is used. Finally a solution of hydroxypropyl methylcellulose phthalate and diethyl phthalate in acetone and ethyl alcohol is used for the enteric coating being applied as the third coating. Also in this case the omeprazole is subjected to an aqueous environment during the preparation of the formulation.

A further number of examples of prior art wherein omeprazole is subjected to an aqueous environment during the preparation of the formulation is given in the following.

According to WO 93/25204 a dry mixture of omeprazole, mannitol, sodium lauryl sulfate and carboxy methyl starch is applied to neutral cores of sugar and starch by means of a binder solution of hydroxypropyl methylcellulose in a mixture of water and ethanol, each application being followed by a drying step. Also protective layers of mannitol applied using the same aqueous hydroxypropyl methylcellulose binder solution as above, saccharose syrup and an enteric coating of hydroxypropyl methylcellulose phthalate are provided.

According to ES 2 087 823, gastro-resistant omeprazole micro-granule formulations are prepared by coating neutral inert granules with a mixture of omeprazole, a diluent such as lactose, saccharose, mannitol or sorbitol, and a surfactant such as sodium lauryl sulfate, using an aqueous-alcoholic solution of polyvinylpyrrolidone (PVP), saccharose and polyethyleneglycol (PEG) as binder. Afterwards a protective coating and a gastro-resistant coating are applied.

PT 101826 describes a process for the preparation of an omeprazole containing micro-granule, formulation, whereby an inert nucleus of starch and saccharose is coated with an active layer containing micronized omeprazole and alkaline sodium salts. The active layer is applied as an aqueous suspension, optionally containing other components like surfactants, binders and disintegrants. The active layer is in turn coated with a water-soluble isolating layer and a gastro-resistant or enteric coating.

WO 96/37195 describes an omeprazole formulation containing $TiO_2$ for stabilisation. The stated purpose is to obtain a stable pharmaceutical formulation having a core containing omeprazole and a single coating, only. The $TiO_2$ is added to the omeprazole containing core and optionally also to the enteric coating. The formulation is obtained by application of an aqueous suspension containing $TiO_2$ and various auxiliary agents, such as binders, sedimentation retarding agents and pH correcting substances, as well as a decreasing amount of omeprazole to an initial core, so that the mixture to be applied by the end contains practically no omeprazole. After drying an enteric coating is applied.

It is observed that the formulation used in the test for stability includes a substantive amount of the alkaline substance, disodium hydrogen phosphate, being known as a stabilizer to omeprazole, in addition to the $TiO_2$.

Finally EP 0 630 235 B1 describes a process for the preparation of sustained release pellets whereby a mixture containing a drug in finely divided form and a wax-like binder substance with a melting point above 40° C. is pelletized by mechanically working the mixture in a high shear mixer under input of a sufficient amount of energy for the binder to melt and the pellitization to take place.

The process is said to be of potential use for any drug that is to be administered orally in order to maintain predetermined blood levels throughout the day. Omeprazole is mentioned as a possible candidate, but none of the working examples relates to the preparation of an omeprazole containing formulation.

As illustrated by the above listing of prior art, many suggestions have been made regarding the preparation of formulations containing omeprazole and other acid labile benzimidazoles for oral administration.

Nevertheless, the present invention provides a new approach for the preparation of oral pharmaceutical formulations comprising a 2-[[(2-pyridinyl)methyl]sulfinyl] benzimidazole having anti-ulcer activity, whereby the benzimidazole can be incorporated in the formulation without the use of water or organic solvents being known to be detrimental to the stability of the benzimidazole, particularly omeprazole, while maintaining an adequate dissolution to allow sufficient absorption within the narrow absorption window for the benzimidazole in the intestine.

This goal is achieved using a melt coating technique to provide preformed cores, such as nonpareils made from saccharose and starch, with a coating layer comprising the benzimidazole, a disintegrant and a surfactant in a matrix of a melt coating substance essentially consisting of one or more esters of glycerol and fatty acids.

Furthermore an enteric coating layer is provided as an outer coating and an intermediate coating layer is provided for protecting the benzimidazole against degradation by the ingredients of the enteric coating.

When this technique is used in accordance with the invention, there is no need to use any alkaline compounds or salts for further stabilization of the benzimidazole. Hereby the risk of attack of the enteric coating from the inside due to alkaline compounds leaching out from the core is avoided.

Accordingly the present invention provides an oral pharmaceutical formulation comprising a 2-[[(2-pyridinyl) methyl]sulfinyl]benzimidazole having anti-ulcer activity as active ingredient, said formulation comprising granules having a substantially inert core coated with i) an inner coating layer comprising the benzimidazole, a disintegrant and a surfactant in a matrix of a melt coating substance essentially consisting of one or more esters of glycerol and fatty acids, ii) an outer coating layer being an enteric coating, and iii) an intermediate coating layer separating the enteric coating layer from the inner coating layer for protection of the benzimidazole against degradation by the ingredients of the enteric coating.

Initial experiments aiming at preparing omeprazole containing formulations for oral administration using a melt pelletizing technique like the one described in EP 0 630 235 B1 for the preparation of omeprazole containing cores were abandoned because of inadequate dissolution properties of the resulting formulation.

However, it has now been discovered that by basing the formulation on granules having a substantially inert core coated with an inner coating layer comprising the benzimidazole, a disintegrant and a surfactant in a matrix of a melt coating substance essentially consisting of one or more esters of glycerol and fatty acids, an omeprazole formulation showing adequate pharmacological properties being comparable to those of the commercial omeprazole product which is marketed under the trade mark Losec®, can be obtained. (Losec® is provided as gelatine capsules which, according to information available from the package, contain enteric coated granules comprising omeprazole, mannitol, hydroxypropyl cellulose, microcrystalline cellulose, anhydrous lactose, sodium lauryl sulfate, di-sodium phosphate dihydrate, hydroxypropyl methylcellulose, methacrylic acid copolymer, Macrogol 400 (polyethylene glycol 400), magnesium stearate, titanium dioxide and iron oxide.)

The esters of glycerol and fatty acids used as the melt coating substance forming the matrix for the benzimidazole containing layer in the formulation according to the invention are natural or synthetic substances being degradable through the normal fat metabolism system in the organism.

The matrix has the function of holding the ingredients of the inner coating layer together in a unified, but not necessarily compact layer. The fatty nature of the melt coating substance means that in addition to having the effect of binding the particles of the other ingredients in the layer together, the melt coating substance will have the effect of coating the particles with a thin layer protecting them against moisture until it has been degraded in the gastrointestinal canal.

A preferred ingredient for the melt coating substance is a fat of the type designated "hard fat" or "adeps solidus", which, according to the European Pharmacopoeia 1997, consists of a mixture of triglycerides, diglycerides and monoglycerides, which may be obtained either by esterification of fatty acids of natural origin with glycerol or by transesterification of natural fats, and has a melting point of 30–45° C. A common use of hard fat is as suppository base.

A further preferred ingredient for the melt coating substance is glyceryl monostearate and particularly glyceryl monostearate 40–50, which is preferably used in combination with hard fat. According to the above Pharmacopoeia, glyceryl monostearate 40–50 is a mixture of monoacylglycerol, chiefly stearoyl- and palmitoylglycerol, together with various quantities of di- and triacylglycerols. It has a melting point of 54–64° C., and contains not less than 40.0 per cent and not more than 50.0 per cent of monoacylglycerols, calculated as dihydroxypropyl monostearate.

The ratio by weight between hard fat and glyceryl monostearate 40–50, when used in the formulation according to the invention, is typically in the range from 100:1 to 1:2 an preferably in the range from 20:1 to 5:2.

In view of the heat sensitive nature of e.g. the omeprazole, the use of melt coating substances of higher melting points should preferably be avoided. On the other hand, the melting point of the melt coating substance should not be so low as to present difficulties during the handling of the formulation. Accordingly, the melting point of the melt coating substance will typically be in the range from 30–60° C., particularly in the range from 30–50° C., and more particularly in the range from 35–45° C. Melt coating substances having a melting point in the vicinity of the body temperature of about 37° C. are particularly preferred from the point of view, that they are very easily absorbed in the intestine.

The benzimidazole will be included in the formulation in a finely divided form and preferably in micronized form. The particle size will typically be <50 μm, and preferably <25 μm, such as <20 μm or even <10 μm.

A disintegrant is incorporated in the matrix so as to allow the building-up of a benzimidazole containing layer of appropriate thickness while maintaining an adequate dissolution rate of the active ingredient, once the enteric coating has been dissolved in the small intestine. Furthermore a surfactant is added.

The disintegrant used in the matrix is preferably of the so-called superdisintegrant type, disintegrants of this type being well-known to the person skilled in the art. As examples of these disintegrants the following can be mentioned: cross-linked polyvinylpyrrolidones, particularly crospovidone, modified starches, particularly sodium starch glycolate, modified celluloses, particularly croscarmellose sodium (cross-linked sodium carboxymethylcellulose) and LHPC (low substituted hydroxypropyl cellulose).

Croscarmellose sodium is e.g. commercialized under the trade name Ac-Di-Sol and sodium starch glycolate under the trade names Primojel and Explotab. Kollidon CL and Polyplasdone XL are commercial crospovidone products.

In a presently preferred embodiment crospovidone is used as disintegrant.

The surfactant used in the matrix will typically be of the non-ionic or anionic type, such as Polysorbate 80 or sodium lauryl sulfate, the latter being a presently preferred surfactant for said use.

The substantially inert cores used in the formulation according to the invention will typically be of a substantially spherical shape and of a substantially uniform size in order to provide a well-defined surface for the coating layer incorporating the active ingredient, although cores of other shapes and mixtures of cores of different sizes may be used as long as they provide a formulation of adequate properties. The cores should be prepared from substantially inert materials, such as materials selected from sugars, starches, modified starches, polymers and combinations thereof.

In a preferred embodiment the saccharose and starch based cores of substantially spherical shape being commercialised under the designation, nonpareils, are used. Such products can e.g. be obtained under the trade mark, Nu-Pareil®. These products are offered in different sizes, usually referring to the US Standard Sieve No. The sizes will typically be in the range from 200–1500 μm, the Mesh sizes 14/18, 16/20, 18/20, 20/25, 25/30 and 30/35 referring to particle sizes in the ranges from 1400–1000, 1180–850, 1000–850, 850–710, 710–610 and 600–500, respectively. In a presently preferred embodiment, cores having a size in the range from 850–1000 μm are used.

As is generally known in the art, an outer enteric coating is provided for protecting the formulation against degradation in the stomach.

Cellulose acetate phthalate, hydroxypropyl methyl cellulose phthalate, hydroxypropyl methylcellulose acetate succinate, polyvinyl acetate phthalate, cellulose acetate trimellitate, carboxymethyl ethylcellulose, various methacrylic acid copolymers such as methacrylic acid/methylmethacrylate copolymers and shellac are non-limiting examples of materials which ay be of use for such purpose.

If desired, various auxiliary agents such as plasticizers, pigments, lubricants etc. may be added. Triethyl citrate and other citric acid esters, phthalic acid esters, dibutyl sebacate, triacetin, cetyl alcohol, polyethylene glycols and polysorbates are non-limiting examples of substances which may be of use for such purpose. Titanium oxide and ferric oxide may be mentioned as non-limiting examples of suitable pigments and talc and silicium dioxide as non-limiting examples of suitable lubricants for use in the enteric coating.

In a presently preferred embodiment the enteric coating layer comprises a copolymer of methacrylic acid and methylmethacrylate in combination with triethyl citrate and micronized talc.

An intermediate coating layer is provided for protecting the omeprazole against degradation by the ingredients of the enteric coating. As non-limiting examples of materials which may be of use for such purpose, hydroxypropyl methylcellulose, hydroxy propyl cellulose and polyvinylpyrrolidone can be mentioned. If desired, various auxiliary agents such as plasticizers, pigments, lubricants etc. as mentioned above, may be added.

In a presently preferred embodiment, the intermediate coating layer comprises hydroxypropyl methylcellulose in combination with titanium dioxide and micronized talc.

However, the intermediate coating layer may also comprise a layer of the melt coating substance essentially consisting of one or more esters of glycerol and fatty acids, optionally including auxiliary agents such as a disintegrant and/or a surfactant, but without the benzimidazole, said layer being provided either as the sole intermediate coating layer or as a supplementary layer.

The relative amounts, by weight, of the ingredients in the formulation according to the invention will typically be as indicated in Table 1 below, wherein also preferred amounts have been indicated, the total amount of the ingredients mentioned in the table and any other ingredients being present in the granules being 100%:

TABLE 1

| Ingredient | Typical | Preferred |
| --- | --- | --- |
| Benzimidazole | 3–20% | 10–15% |
| Surfactant | 0.5–10% | 1.5–5.0% |
| Disintegrant | 0.5–15% | 2.5–10.0% |
| Inert cores | 60–90% | 70–80% |
| Glycerol ester | 2–15% | 3–10% |

In a preferred embodiment, the formulation according to the invention is dispensed in gelatine capsules, each capsule typically containing a unit dose, such as a dose of 10, 20 or 40 mg of omeprazole, 40 mg of pantoprazole or 15 or 30 mg of lansoprazole. The doses specifically mentioned correspond to the doses contained in the capsule preparations being marketed at present.

The invention also relates to a process for the preparation of an oral pharmaceutical formulation as stated above, said process comprising the step of providing substantially inert cores with a coating layer comprising the benzimidazole, a disintegrant and a surfactant in a matrix of a melt coating substance essentially consisting of one or more esters of glycerol and fatty acids, by a melt coating technique.

Particularly the invention relates to a process comprising the steps of
i) mixing the benzimidazole with the surfactant and the disintegrant,
ii) blending the mixture obtained in step i) with the substantially inert cores while heating to a temperature above the melting point of the melt coating substance,
iii) adding the melt coating substance to the blend obtained in step ii) while blending and heating to a temperature above the melting point of the melt coating substance,
iv) continuing the blending and heating to a temperature above the melting point of the melt coating substance until an adequate coating of the cores has been obtained, and
v) cooling the coated cores obtained i step iv) to room temperature.

The substantially inert cores are preferably heated to a temperature above the melting point of the melt coating substance before the blending in step ii), the coating process thereby being facilitated. Normally a temperature 0–20° C. and particularly 5–15° C. above the melting point of the melt coating substance will be adequate.

The melt coating substance can be added as a melt in step iii) or it can be added as a solid, e.g. as a finely divided solid, such as fine flakes. In a presently preferred embodiment it is added as a melt.

When an adequate coating of the cores has been obtained, the coated cores are cooled to room temperature. The cooling may be carried out in one or more steps. In a presently preferred embodiment, the cooling is carried out in two steps, the first step being carried out under continued blending until a temperature slightly above the melting point of the melt coating substance has been reached, and the second step being carried out by tray cooling.

In a particular embodiment, the process comprises the further steps of coating the obtained substantially inert cores coated with the coating layer comprising the benzimidazole, a disintegrant and a surfactant in a matrix of a melt coating substance, with an intermediate coating layer and an outer coating layer, the outer coating layer being an enteric coating and the intermediate coating layer being adapted for protection of the omeprazole against degradation by the ingredients of the enteric coating.

Finally the obtained coated granules may be disposed in gelatine capsules, each capsule preferably containing a unit dose, such as a dose of 10, 20 or 40 mg of omeprazole, a dose of 40 mg of pantoprazole or a dose of 15 or 30 mg of lansoprazole.

The invention will now be further described in the following by non-limiting examples.

EXAMPLE 1

A. Coating of inert cores with omeprazole containing layer.

| | | |
|---|---|---|
| I Omeprazole, micronized | 240.0 | g |
| II Sodium lauryl sulfate | 60.0 | — |
| III Kollidon CL (crospovidone) | 100.0 | — |
| IV Nu-Pareil PG 18/20 | 1400.0 | — |
| V Witepsol H 15 *) | 94.1 | — |
| VI Glyceryl monostearate 40–50 | 6.1 | — |
| VII Mixture of V and VI | 75.0 | — |
| VIII Mixture of V and VI | 12.0 | — |

*) Hard fat having a melting point of 35° C.

I, II and III are mixed intensively and heated to a temperature of 40° C., after which IV is blended with I+II+III in a blender preheated to about 40° C., for 30 sec.

75.0 g of a finely divided mixture of V and VI is added to the blender and blended with I+II+III+IV for about 2 min. Product temperature after blending: 43° C.

Then further 12.0 g of the finely divided mixture of V and VI is added, and the blending is continued for about 3 min., until a product temperature of 45° C. has been reached.

After further blending for 2 min. at a mantle temperature of 35° C., the product is removed from the blender and transferred to trays for further cooling to room temperature.

B. Coating with Intermediate Layer 250 g of pellets prepared as described under A. are transferred to a combi-coater wherein they are coated with 144.5 g of a coating liquid obtained by mixing of 15 parts of HPMC 5, 6 parts of micronized talc, 6 parts of titanium dioxide and 285 parts of purified water, all parts being parts by weight.

After drying at 30° C. for 30 min., the product is cooled to room temperature and weighed.

C. Coating with Enteric Coating

The coated pellets obtained under B. are coated with 250 g of a freshly prepared coating liquid obtained by mixing a mixture of 22.5 parts of micronized talc, 0.5 parts of anti-foaming emulsion, 4.5 parts of Citroflex 2 (triethyl citrate) and 78 parts of purified water, with a mixture of 135 parts of Eudragit L 30 D-55 (an aqueous dispersion of a methacrylic acid-methyl methacrylate copolymer) and 60 parts of purified water, all parts being parts by weight.

EXAMPLE 2

A. Coating of inert cores with omeprazole containing layer.

| | | |
|---|---|---|
| I Omeprazole, micronized | 2880.0 | g |
| II Sodium lauryl sulfate | 720.0 | — |
| III Kollidon CL | 1200.0 | — |
| IV Nu-Pareil PG 18/20 | 16.80 | kg |
| V Witepsol H 15 | 1128.0 | g |
| VI Glyceryl monostearate 40–50 | 72.0 | — |

A mixture of I+II and III obtained by mixing in a blender is added to a blender containing IV, preheated to a temperature of about 40° C., while stirring at 140 rpm, after which the blending is continued for 30 sec. at a heating mantle temperature of 40–45° C.

A liquid mixture of V+VI, heated to 45–50° C. is added while blending at 140 rpm. About 10% of the mixture of V+VI is retained. Blending is carried out for 2 min. at 140 rpm. After scraping of the walls as necessary, blending is continued for 30 sec. The remaining 10% of V+VI is added and the blending is continued for 2 min. Then the mantle temperature is reduced to about 38° C., and blending is continued for 2 min. at 140 rpm.

The product is transferred to trays for cooling at room temperature.

The pellet fraction from 0.8 to 1.25 mm is obtained by screening.

The obtained pellets can be provided with intermediate and enteric coating layers in a similar manner to that described in Example 1.

Pilot Bioequivalence Study

Size 1 gelatine capsules containing 220 mg of granules prepared as described in Example 1 (omeprazole content 20 mg) were compared to commercial Losec® capsules containing 20 mg omeprazole in a randomized single dose cross-over study carried out on 8 healthy males.

The results are shown in the following Table 2, indicating the maximum plasma concentration, $C_{max}$, the time for reaching the maximum plasma concentration, $T_{max}$, and the area below the plasma concentration curve, $AUC_{0-\infty}$, for both products, as well as $F_{rel}$, the ratio between $AUC_{0-\infty}$ for the product according to the invention and $AUC_{0-\infty}$ for the known product. Mean, SD, SEM and CV% values are stated, CV% indicating the standard deviation, SD, as percentage of the mean value.

As will be seen, the bioavailability of the product according to the invention is comparable to that of the known product. However, it also seems as if the variation in bioavailability from person to person is smaller for the product according to the invention than for the known product as indicated by the lower CV% values for $C_{max}$ and $AUC_{0-\infty}$.

TABLE 2

| | Formulation according to invention (A) | | | Losec ® (B) | | | $F_{rel}$ $\dfrac{AUC_{0-\infty}, (A)}{AUC_{0-\infty}, (B)}$ |
|---|---|---|---|---|---|---|---|
| Subjects | $C_{max}$ ng/ml | $T_{max}$ hours | $AUC_{0-\infty}$ (ng/ml) h | $C_{max}$ ng/ml | $T_{max}$ hours | $AUC_{0-\infty}$ (ng/ml) h | |
| 1 | 849.78 | 4.0 | 2672.5 | 933.44 | 2.5 | 4089.5 | 0.65 |
| 2 | 235.18 | 1.5 | 458.6 | 300.96 | 1.0 | 494.0 | 0.93 |
| 3 | 646.57 | 1.0 | 995.7 | 277.73 | 2.5 | 676.5 | 1.47 |
| 4 | 476.54 | 1.0 | 751.6 | 495.37 | 1.5 | 1128.3 | 0.67 |
| 5 | 317.22 | 1.0 | 312.7 | 95.61 | 3.0 | 155.0 | 2.02 |
| 6 | 246.62 | 2.0 | 458.9 | 247.62 | 3.0 | 474.1 | 0.97 |
| 7 | 226.85 | 2.0 | 397.0 | 192.63 | 3.0 | 415.9 | 0.95 |
| 8 | 408.74 | 2.0 | 489.3 | 260.74 | 1.0 | 342.3 | 1.43 |
| Mean | 425.94 | 1.8 | 817.0 | 350.51 | 2.2 | 972.0 | 1.14 |
| SD | 223.98 | 1.0 | 781.4 | 261.07 | 0.9 | 1291.1 | 0.47 |
| SEM | 79.19 | 0.4 | 276.3 | 92.30 | 0.3 | 456.7 | 0.17 |
| CV % | 52.6 | 55.0 | 95.6 | 74.5 | 40.4 | 132.9 | 41.2 |

Dissolution Tests
Determination of Quantitative Content of Omeprazole in Pellets Prepared According to Example 1

Six determinations were carried out. The samples were analyzed by HPLC. The mean value was 8.6 mg of omeprazole per 100 mg of pellets with a relative standard deviation of 3.8%.

Determination of Quantitative Content of Omeprazole in Pellets Prepared According to Example 1, after Stirring in 0.1 N HCl at 37° C. for 120 min.

Six determinations were carried out after stirring of the pellets in 0.1 N HCl at 37° C. for 120 min. The samples were analyzed by HPLC.

No degradation of the omeprazole by the acid was seen. The mean value was 8.7 mg of omeprazole per 100 mg pellets with a relative standard deviation of 4.3%.

Dissolution of Omeprazole from Pellets Prepared According to Example 1, after Stirring in 0.1 N HCl at 37° C. for 120 min.

Six determinations were carried out in a dissolution apparatus at a pH of 7.2 after stirring of the pellets in 0.1 N HCl at 37° C. for 120 min. The samples were analyzed by HPLC.

After 60 minutes more than 89% of the omeprazole content in the pellets was dissolved with a relative standard deviation of 1%.

The dissolution percentages after 15, 30 and 120 min. were 90%, 87% and 85%, respectively.

Dissolution of Omeprazole from Pellets Prepared According to Example 2, after Stirring in 0.1 N HCl at 37° C. for 120 min.

Four batches of enteric coated pellets prepared according to Example 2 were tested for dissolution after stirring in 0.1 N HCl at 37° C. for 120 min. as described above.

The results are indicated in Table 3 below.

TABLE 3

| | Dissolution in %. | | | | |
|---|---|---|---|---|---|
| Batch No. | 0 min. | 15 min. | 30 min. | 60 min. | 120 min. |
| 805302 | 0 | 88 | 91 | 94 | 91 |
| 806001 | 0 | 83 | 85 | 85 | 82 |
| 807001 | 0 | 77 | 81 | 82 | 80 |
| 807601 | 0 | 81 | 89 | 92 | 89 |

In the preceding the invention has been described by means of specific examples of preferred embodiments. However, it will be appreciated that various modifications can be made by a person skilled in the art, without deviating from the spirit and scope of the invention.

What is claimed is:

1. An oral pharmaceutical formulation comprising a 2-[[(2-pyridinyl)methyl]sulfinyl]benzimidazole having antiulcer activity as active ingredient, said formulation comprising granules having a substantially inert core coated with i) an inner coating layer comprising the benzimidazole, a disintegrant and a surfactant in a matrix of a melt coating substance essentially consisting of one or more esters of glycerol and fatty acids, ii) an outer coating layer being an enteric coating, and iii) an intermediate coating layer separating the enteric coating layer from the inner coating layer for protection of the benzimidazole against degradation by the ingredients of the enteric coating.

2. The formulation of claim 1, wherein the melt coating substance has a melting point in the range from 30 to 60° C.

3. The formulation of claim 2, wherein the melt coating substance has a has a melting point in the range from 30 to 50° C.

4. The formulation of claim 3, wherein the melt coating substance has a melting point in the range from 35 to 45° C.

5. The formulation according to claim 1, wherein the melt coating substance consists essentially of a mixture of hard fat and glyceryl monostearate 40–50.

6. The formulation according to claim 5, wherein the ratio by weight between hard fat and glyceryl monostearate 40–50 is in the range from 100:1 to 1:2.

7. The formulation according to claim 5, wherein the ratio by weight between hard fat and glyceryl monostearate 40–50 is in the range from 20.1 to 5:2.

8. The formulation according to claim 1, wherein the disintegrant is a superdisintegrant.

9. The formulation according to claim 8, wherein the superdisintegrant is crospovidone.

10. The formulation according to claim 1, wherein the benzimidazole is micronized.

11. The formulation according to claim 1, wherein the surfactant is an anionic or a nonionic surfactant.

12. The formulation according to claim 11, wherein the surfactant is sodium lauryl sulfate.

13. The formulation according to claim 1, wherein the substantially inert cores are nonpareils made from saccharose and starch and of a size in the range from 200 to 1500 µm.

14. The formulation according to claim 13, wherein the substantially inert cores are of a size in the range from 850 to 1000 µm.

15. The formulation according to claim 1, wherein the enteric coating layer comprises a copolymer of methacrylic acid and methylmethacrylate.

16. The formulation according to claim 15, wherein the enteric coating layer further comprises a plasticizer.

17. The formulation according to claim 16, wherein the plasticizer is triethyl citrate.

18. The formulation according to claim 16, wherein the enteric coating layer further comprises an auxiliary agent.

19. The formulation according to claim 18, wherein the auxiliary agent is micronized talc.

20. The formulation according to claim 1, wherein the intermediate coating layer comprises hydroxypropyl methylcellulose.

21. The formulation according to claim 20, wherein the intermediate coating layer further comprises an auxiliary agent.

22. The formulation according to claim 21, wherein the auxiliary agent is titanium dioxide or micronized talc.

23. The formulation according claim 1, wherein the intermediate coating layer comprises a layer of the melt coating substance consisting essentially of one or more esters of glycerol and fatty acids.

24. The formulation according claim 23, wherein the layer of melt coating substance further comprises an auxiliary agent.

25. The formulation according to claim 24, wherein the auxiliary agent is a disintegrant or a surfactant.

26. The formulation according to claim 1, wherein the benzimidazole is omeprazole, pantoprazole or lansoprozole.

27. The formulation according to claim 1, being provided as a unit dose in a gelatine capsule.

28. The formulation according to claim 27, wherein the unit dose is 10, 20 or 40 mg of omeprazole.

29. The formulation according to claim 27, wherein the unit dose is 40 mg of pantoprazole.

30. The formulation according to claim 27, wherein the unit dose is 15 or 30 mg of lansoprazole.

31. A process for the preparation of an oral pharmaceutical formulation according to claim 1 comprising the step of providing substantially inert cores with a coating layer comprising the benzimidazole, a disintegrant and a surfactant in a matrix of a melt coating substance consisting essentially of one or more esters of glycerol and fatty acids, by a melt coating technique.

32. The process according to claim 31, further comprising the steps of i) mixing the benzimidazole with the surfactant and the disintegrant, ii) blending the mixture obtained in step i) with the substantially inert cores while heating to a temperature above the melting point of the melt coating substances, iii) adding the melt coating substance to the blend obtained in step ii) while blending and heating to a temperature above the melting point of the melt coating substance, iv) continuing the blending and heating to a temperature above the melting point of the melt coating substance until an adequate coating of the cores has been obtained, and v) cooling the coated cores obtained in step iv) to room temperature.

33. The process according to claim 32, wherein the melt coating substance is added as a melt in step (iii).

34. The process according to claim 32, wherein the melt coating substance is added as a finely divided solid in step (iii).

35. The process according to claim 32, wherein the cooling to room temperature in step v) is carried out in two steps, the first step being carried out under continued blending until a temperature slightly above the melting point of the melt coating substance has been reached, and the second step being carried out by tray cooling.

36. The process according to claim 31, comprising the further steps of coating the obtained substantially inert cores, coated with the coating layer comprising the benzimidazole, a disintegrant and a surfactant in a matrix of a melt coating substance, with an intermediate coating layer and an outer coating layer, the outer coating layer being an enteric coating and the intermediate coating layer being adapted for protection of the benzimidazole against degradation by the ingredients of the enteric coating.

37. The process according to claim 32, comprising the further steps of coating the obtained substantially inert cores, coated with the coating layer comprising the benzimidazole, a disintegrant and a surfactant in a matrix of a melt coating substance, with an intermediate coating layer and an outer coating layer, the outer coating layer being an enteric coating and the intermediate coating layer being adapted for protection of the benzimidazole against degradation by the ingredients of the enteric coating.

* * * * *